(12) United States Patent
Monaco

(10) Patent No.: US 11,576,810 B1
(45) Date of Patent: Feb. 14, 2023

(54) ENHANCED SEXUAL TRANSMISSION PREVENTION DEVICE

(71) Applicant: Donato Monaco, Orlando, FL (US)

(72) Inventor: Donato Monaco, Orlando, FL (US)

( * ) Notice: Subject to any disclaimer, the term of this patent is extended or adjusted under 35 U.S.C. 154(b) by 0 days.

(21) Appl. No.: 16/774,563

(22) Filed: Jan. 28, 2020

Related U.S. Application Data

(60) Provisional application No. 62/818,394, filed on Mar. 14, 2019.

(51) Int. Cl.
*A61F 6/04* (2006.01)

(52) U.S. Cl.
CPC .......... *A61F 6/04* (2013.01); *A61F 2006/047* (2013.01)

(58) Field of Classification Search
CPC ...... A61F 2006/047; A61F 6/04; A61F 6/065; A61F 2006/042; Y10S 128/918; A61H 19/32
See application file for complete search history.

(56) References Cited

U.S. PATENT DOCUMENTS

| | | |
|---|---|---|
| 4,781,709 A | 11/1988 | Grubman |
| 4,834,113 A * | 5/1989 | Reddy ....................... A61F 6/04 128/830 |
| 4,872,464 A | 10/1989 | Loeb et al. |
| 4,981,147 A | 1/1991 | Barnett |
| 5,069,228 A | 12/1991 | Sorkin |
| 5,083,414 A * | 1/1992 | Wu ......................... A61F 6/005 128/844 |
| 5,168,881 A | 12/1992 | Reddy |
| 5,419,341 A | 5/1995 | Galasso |
| 5,649,549 A * | 7/1997 | Saba ......................... A61F 6/06 128/842 |
| 5,749,862 A | 5/1998 | Lau |
| 8,839,792 B2 | 9/2014 | Brunner |
| D737,422 S | 8/2015 | Ward, Jr. II |
| D737,423 S | 8/2015 | Mulson |
| D757,241 S | 5/2016 | Agha |
| 2007/0272253 A1 | 11/2007 | Lin |
| 2008/0135055 A1 | 6/2008 | Portnoff |
| 2010/0071702 A1 * | 3/2010 | Sturlingh .................. A61F 6/04 128/844 |
| 2015/0157493 A1 | 6/2015 | Agha |
| 2016/0051399 A1 * | 2/2016 | Tang ................... B29C 66/0326 128/830 |

* cited by examiner

*Primary Examiner* — Ophelia A Hawthorne
(74) *Attorney, Agent, or Firm* — John Rizvi, P.A.

(57) ABSTRACT

An enhanced sexual transmission prevention device is disclosed. The device is a condom cover for the groin area with adhesive edges and a central aperture through which a male member is inserted. The aperture is designed to help secure the rolled up portion of a condom to the base of male member, preventing the condom from slipping off. The device also goes over the condom and, with adhesive, attaches to the male body so that the groin area surrounding the male member is protected from skin-to-skin transmission of sexually transmitted infections. The enhanced sexual transmission prevention device is comprised of a resilient material, similar to a condom, so that the two devices may work together effectively. In one embodiment the enhanced sexual transmission prevention device incorporates the condom itself, for ease of use and wearing.

20 Claims, 9 Drawing Sheets

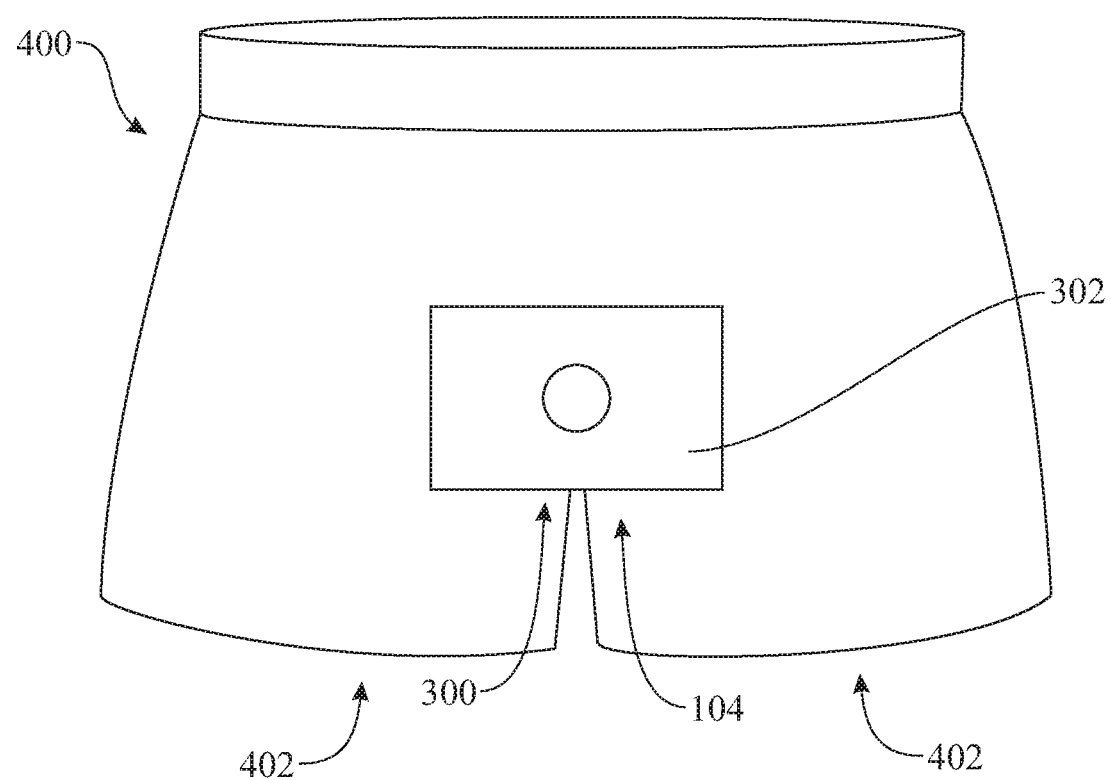

ENHANCED SEXUAL TRANSMISSION PREVENTION DEVICE

CROSS-REFERENCE TO RELATED APPLICATIONS

This application claims the benefit of U.S. Provisional Patent Application No. 62/818,394, filed on Mar. 14. 2019, which is incorporated herein in its entirety.

FIELD OF THE INVENTION

The present invention relates generally to personal hygiene devices, and more particularly, to an enhanced sexual transmission prevention device.

BACKGROUND OF THE INVENTION

Sexually transmitted infections (STI), also referred to as sexually transmitted diseases (STD), are infections that are commonly spread by sexual activity, especially vaginal intercourse, anal sex, and oral sex. Many STIs initially do not cause symptoms, which results in a greater risk of passing the disease on to others. Symptoms and signs of disease may include vaginal discharge, penile discharge, ulcers on or around the genitals, and pelvic pain. STIs can be transmitted to an infant before or during childbirth and may result in poor outcomes for the baby. Some STIs may even cause problems with the ability to get pregnant.

A condom is a sheath-shaped barrier device, used during sexual intercourse to reduce the probability of pregnancy or STI. There are both male and female condoms. With proper use, and use at every act of intercourse, women whose partners use male condoms experience a 2% per-year pregnancy rate. Their use greatly decreases the risk of gonorrhea, chlamydia, trichomoniasis, hepatitis B, and HIV/AIDS. They also, to a lesser extent, protect against genital herpes, HPV, and syphilis.

The male condom is rolled onto an erect male member before intercourse and works by blocking semen from entering the body of a sexual partner, and by blocking some (but not all) skin to skin contact. Male condoms are typically made from latex and, less commonly, from polyurethane or lamb intestine. Male condoms have the advantages of ease of use, ease of access, and few side effects. In those users with a latex allergy, a polyurethane or other synthetic version should be used.

Male condoms, though, only cover the shaft of the male member itself and provide no protection for the general groin area surrounding the base of the male member. Also, male condoms, especially when too large for a user, can slip off the shaft of the male member during sexual intercourse. Further, a condom may fall off if the wearer starts to lose their erection. Because the skin of the groin area is thinner and more sensitive it also is less resistant to the transmission of STIs by skin-to-skin contact, and the use of a male condom alone does not protect this vital area.

Therefore, there is a need in the art for an enhanced sexual transmission prevention device that may enhance the effectiveness of a male condom by protecting the groin area from skin-to-skin transmission of STIs while preventing the condom from slipping off the male member during sexual intercourse.

SUMMARY OF THE INVENTION

This summary is provided to introduce a selection of concepts in a simplified form that are further described below in the detailed description. This summary is not intended to identify key features of essential features of the claimed subject matter, nor is it intended to be used to limit the scope of the claimed subject matter. Furthermore, the claimed subject matter is not limited to implementations that solve any or all disadvantages noted in any part of this disclosure.

According to embodiments of the present disclosure, an enhanced sexual transmission prevention device is disclosed.

In one aspect, the enhanced sexual transmission prevention device may comprise a compact design.

In another aspect, the enhanced sexual transmission prevention device may comprise a one-piece design.

In another aspect, the enhanced sexual transmission prevention device may comprise a resilient material of construction.

In another aspect, the enhanced sexual transmission prevention device may comprise a wearable device.

In another aspect, the enhanced sexual transmission prevention device may comprise an elastic circumferential interference seal.

In another aspect, the enhanced sexual transmission prevention device may comprise a fluid-resistant material of construction.

In another aspect, the enhanced sexual transmission prevention device may comprise a tear-resistant material of construction.

In another aspect, the enhanced sexual transmission prevention device may comprise a practical design.

In another aspect, the enhanced sexual transmission prevention device may comprise a manufacturable design.

In another aspect, the enhanced sexual transmission prevention device may comprise an inexpensive design.

In another aspect, the enhanced sexual transmission prevention device may comprise an easy-to-use design.

In another aspect, the enhanced sexual transmission prevention device may comprise a foldable design.

In another aspect, the enhanced sexual transmission prevention device may comprise a die-cut manufacturing process.

In another aspect, the enhanced sexual transmission prevention device may comprise a garment.

These and other objects, features, and advantages of the present invention will become more readily apparent from the attached drawings and the detailed description of the preferred embodiments or examples, which follow.

BRIEF DESCRIPTION OF THE DRAWINGS

The preferred embodiments and examples of the claimed subject matter will hereinafter be described in conjunction with the appended drawings provided to illustrate and not to limit the scope of the claimed subject matter, where like designations denote like elements, and in which:

FIG. 10 illustrates an alternative embodiment of an enhanced sexual transmission prevention device, in accordance with aspects of the present disclosure.

It is to be understood that like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. Furthermore, there is no intention to be bound by any expressed or implied theory presented in the preceding technical field, background, brief summary, or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

The illustrations of FIGS. 1 through 5 illustrate wearing an enhanced sexual transmission prevention device. As contemplated by the present disclosure, the enhanced sexual transmission prevention device comprises, generally, a resilient material sheet having a central opening and a plurality of adhesive strips to be worn over a male condom on the male member of a user. The device is intended to be simple, cost effective, and easy to use so that it is not inconvenient for a user to implement such additional sexual transmission prevention. It is to be understood that any number of adhesive strips may be added to any number of sides of the device, such as on all four edges. Therefore, the number of adhesive strips should not be limited by the number of shown adhesive strips in the figures.

Figure 1:
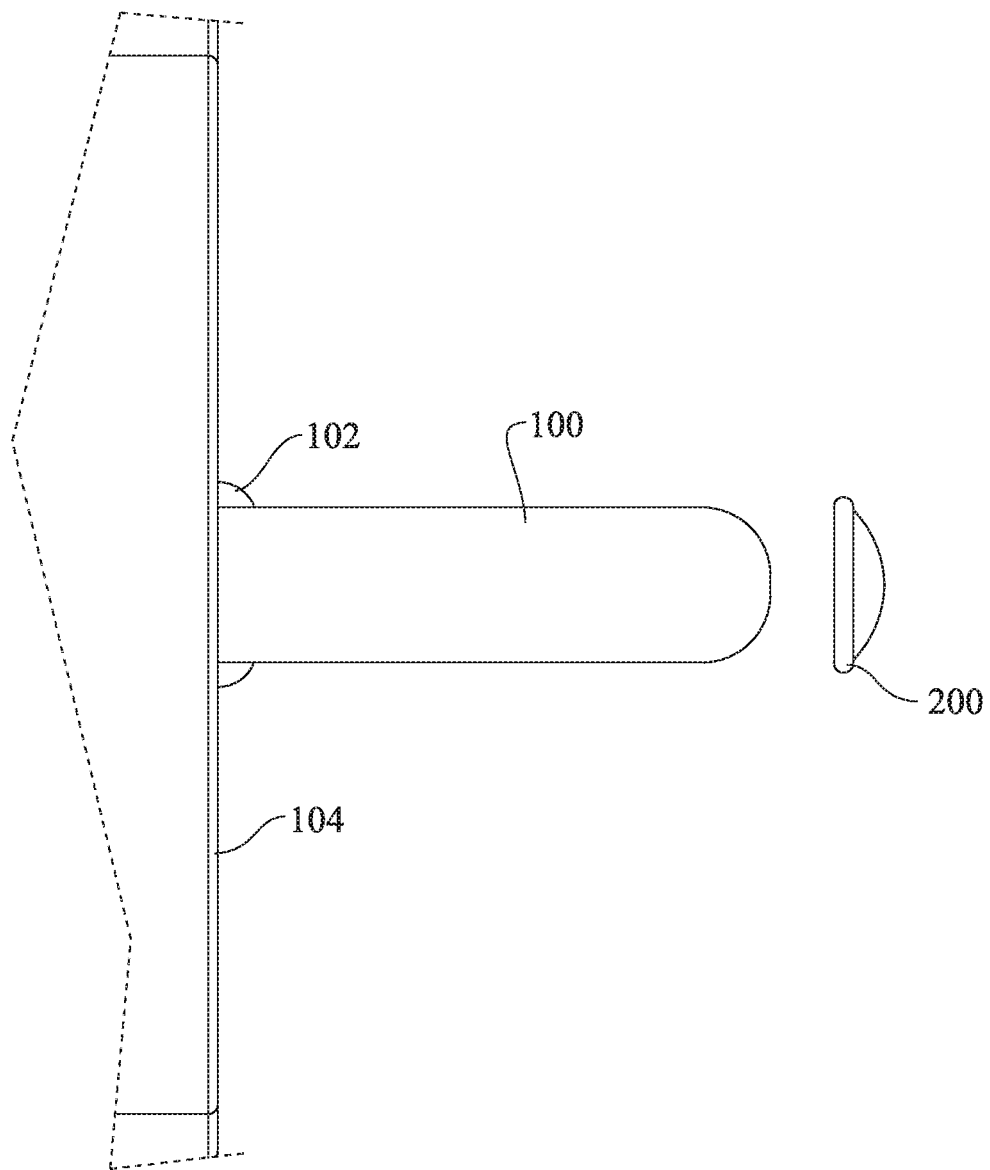
FIG. 1 illustrates a male member prior to the wearing of a male condom, in accordance with aspects of the present disclosure.

The illustration of FIG. 1 illustrates, in particular, a generic male member 100 from a top perspective view with an unworn condom. The male member 100 extends from left to right, with a scrotum 102 illustrated at its base, with both structures attached to a groin area 104 of a user. The figure also shows a rolled up condom 200 ready to be donned over the male member 100 of the user, which comprises the first step of the process that involves wearing e enhanced sexual transmission prevention device.

Figure 2:
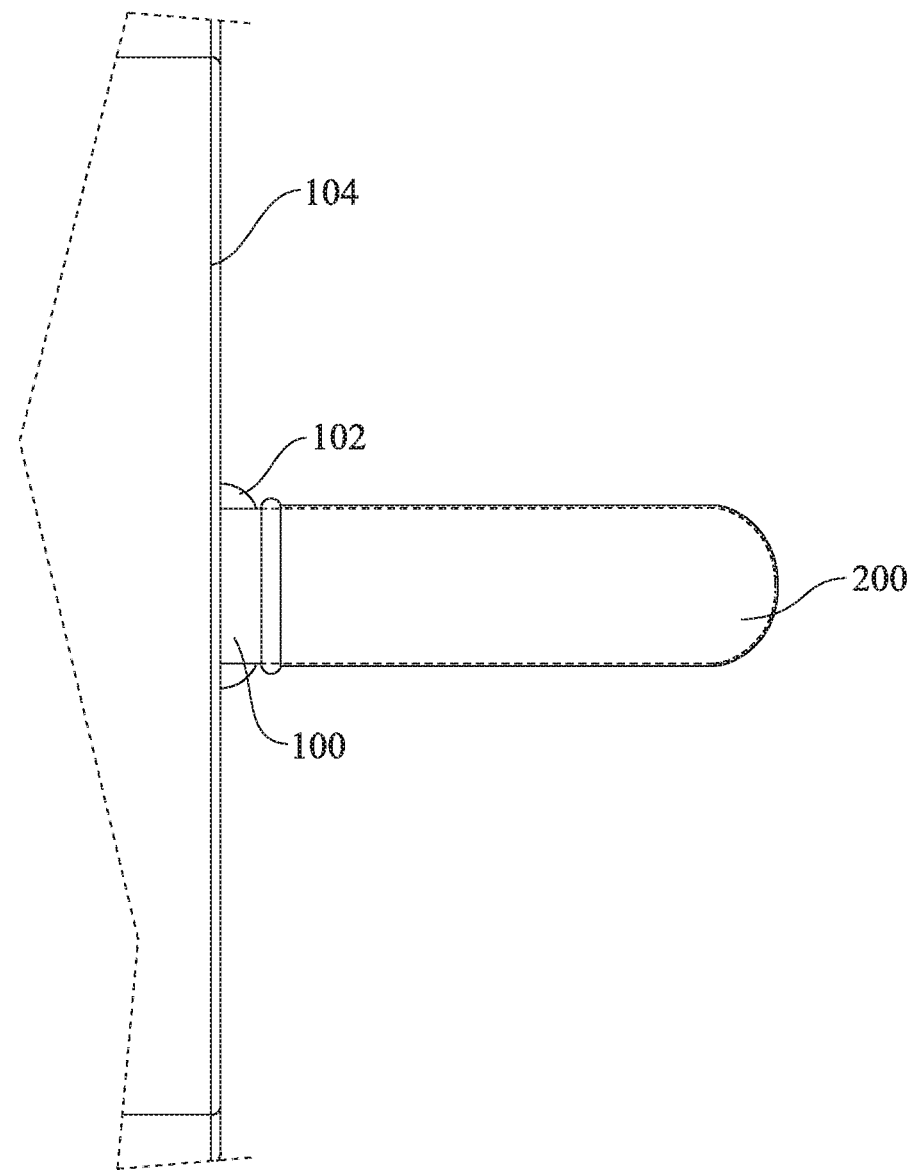
FIG. 2 illustrates a male member wearing a male condom, in accordance with aspects of the present disclosure.

The illustration of FIG. 2 illustrates, in particular, a generic male member 100 from a top perspective view with a worn condom. The male member 100 extends from left to right, with a scrotum 102 illustrated at its base, with both structures attached to a groin area 104 of a user. The figure also shows an unrolled condom 200 already installed on the male member 100 of the user, which comprises the second step of the process involved in wearing the enhanced sexual transmission prevention device. The condom is shown covering the head and shaft of the male member 100, though it does not also cover the scrotum 102 nor extend to the groin area 104 of the user.

Figure 3:
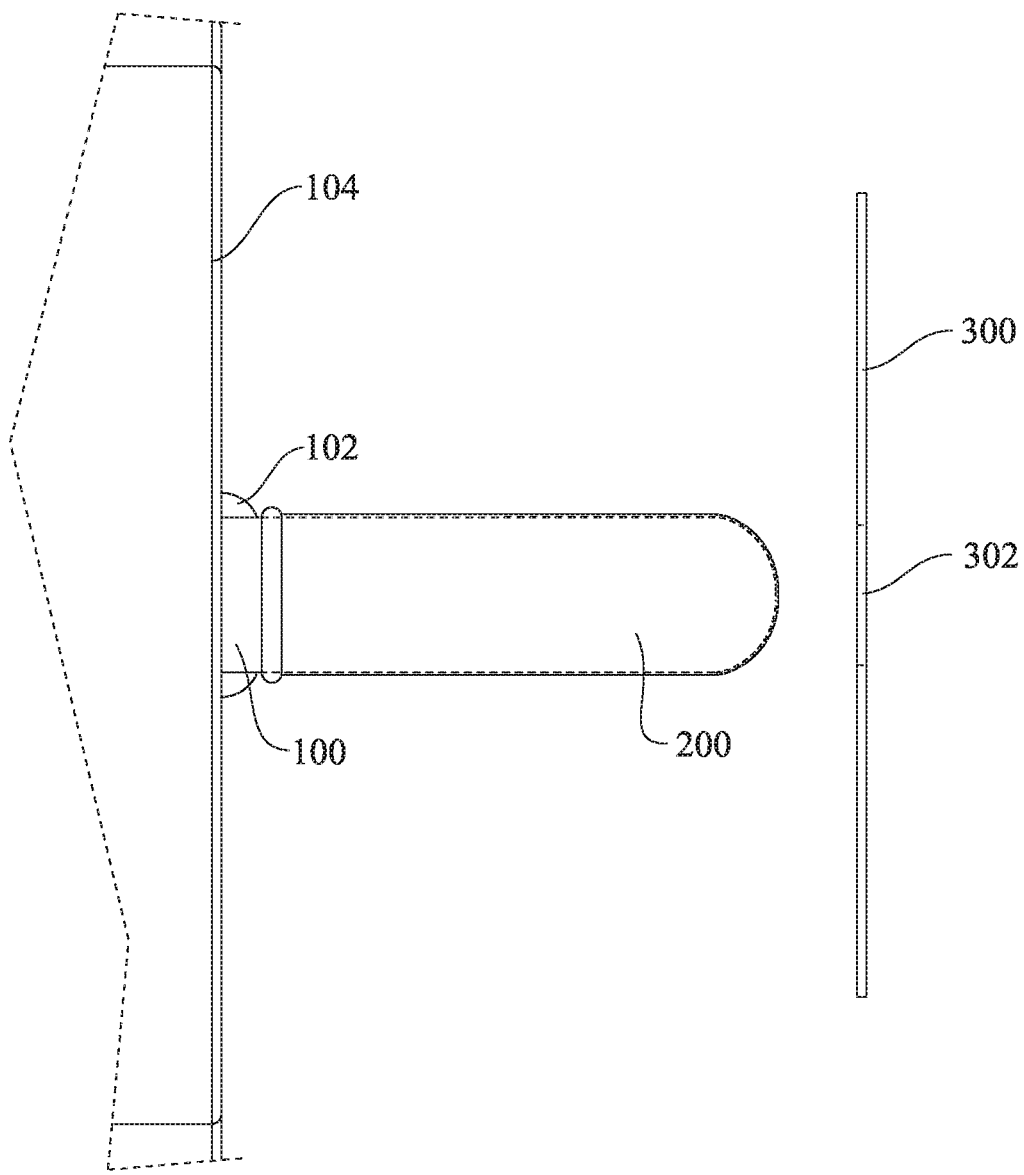
FIG. 3 illustrates a first step for wearing an enhanced sexual transmission prevention device, in accordance with aspects of the present disclosure.

The illustration of FIG. 3 illustrates, in particular, a generic male member 100 from a top perspective view with a worn condom and the enhanced sexual transmission prevention device. The male member 100 extends from left to right, with a scrotum 102 illustrated at its base, with both structures attached to a groin area 104 of a user, and an unrolled condom 200 is already installed on the male member 100 of the user. The resilient material sheet 300 of the enhanced sexual transmission prevention device is placed near the tip of the male member 100 such that the tip of the male member 100 may be inserted into the central opening 302 of the resilient material sheet 300, which comprises the third step of the process involved in wearing the enhanced sexual transmission prevention device. The condom is shown covering the head and shaft of the male member 100, though it does not also cover the scrotum 102 nor extend to the groin area 104 of the user. The resilient material sheet 300, once installed is intended to cover the scrotum 102 and the groin area 104 of the user to provide enhanced sexual transmission prevention.

Figure 4:
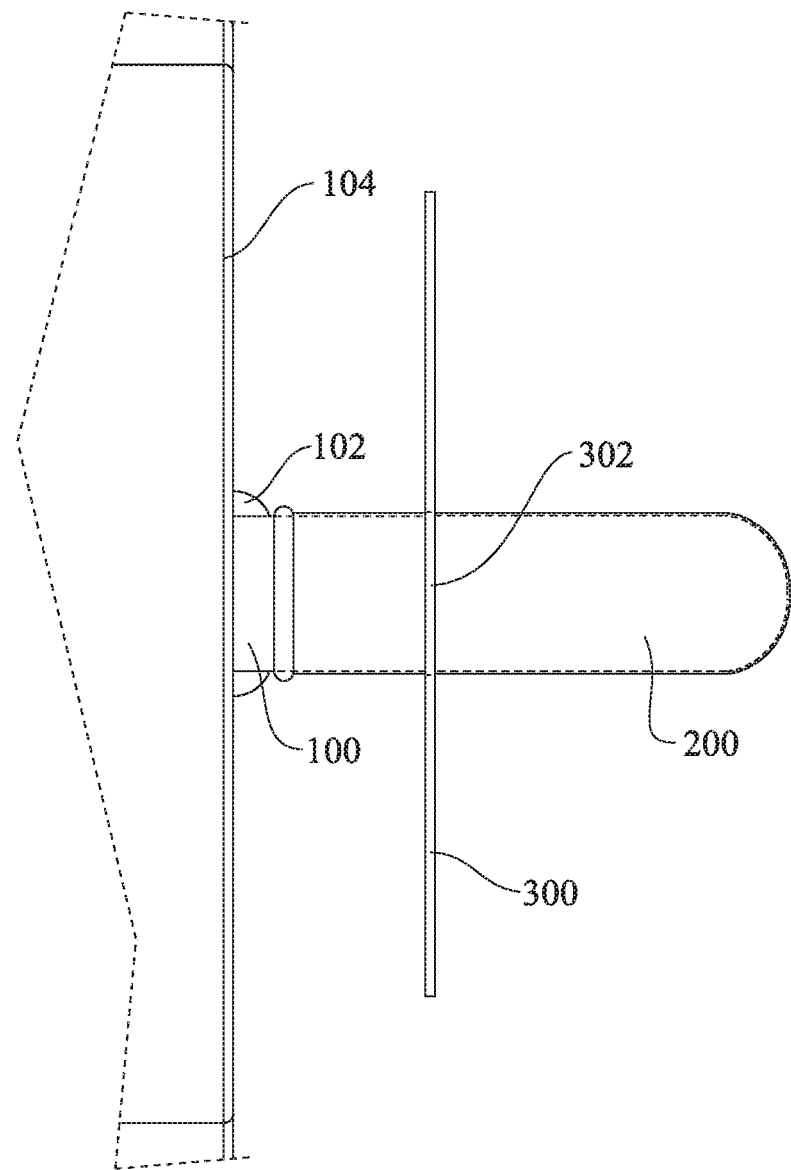
FIG. 4 illustrates a second step for wearing an enhanced sexual transmission prevention device, in accordance with aspects of the present disclosure.

The illustration of FIG. 4 illustrates, in particular, a generic male member 100 from a top perspective view with a worn condom and the enhanced sexual transmission prevention device partially installed. The male member 100 extends from left to right, with a scrotum 102 illustrated at its base, with both structures attached to a groin area 104 of a user, and an unrolled condom 200 is already installed on the male member 100 of the user. The tip of the male member 100 is passed through the central opening 302 of the resilient material sheet 300, and the resilient material sheet 300 is then pulled along the shaft of the male member 100 towards the groin area 104 of the user, which comprises the fourth step of the process involved in wearing the enhanced sexual transmission prevention device. The condom is shown covering the head and shaft of the male member 100, though it does not also cover the scrotum 102 nor extend to the groin area 104 of the user. The resilient material sheet 300 is pulled towards the groin area 104 of the user and may cover the scrotum 102 and the groin area 104 of the user, once properly installed, to provide enhanced sexual transmission prevention.

Figure 5:
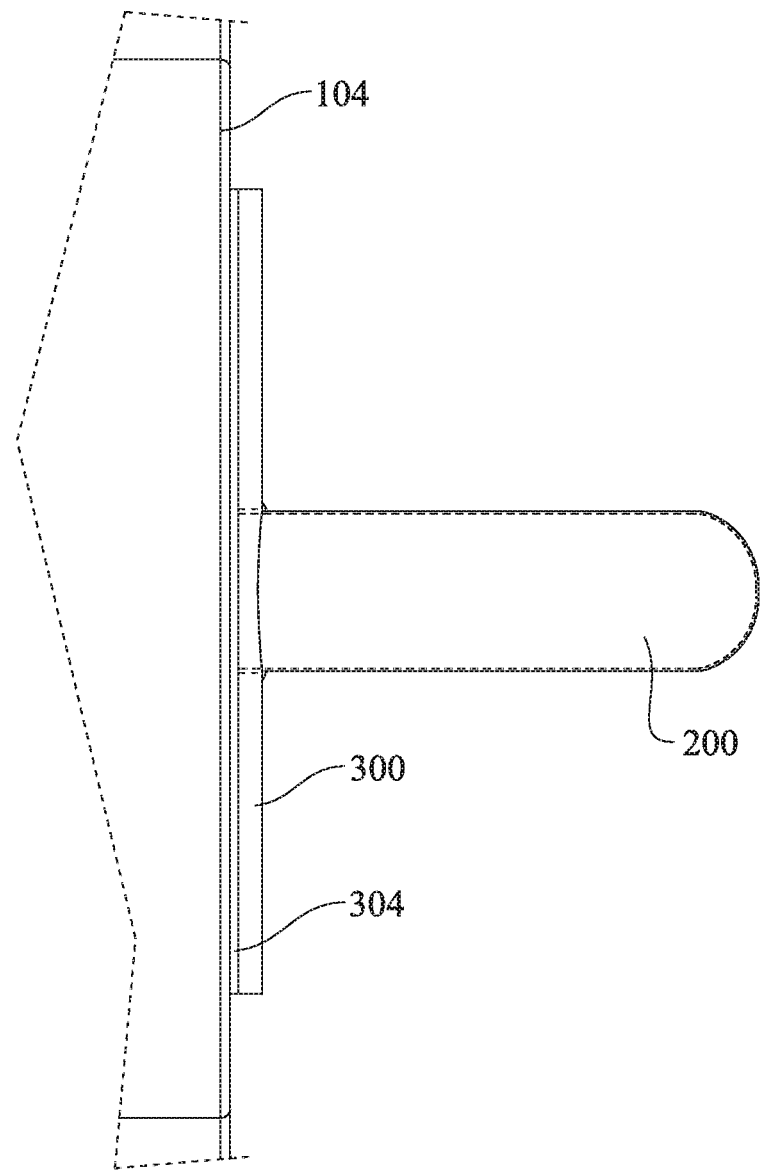
FIG. 5 illustrates a third step for wearing an enhanced sexual transmission prevention device, in accordance with aspects of the present disclosure.

The illustration of FIG. 5 illustrates, in particular, a generic male member 100 from a top perspective view with a worn condom and the enhanced sexual transmission prevention device fully installed. The male member 100 extends from left to right, with a scrotum 102 illustrated at its base, with both structures attached to a groin area 104 of a user, and an unrolled condom 200 is already installed on the male member 100 of the user. The tip of the male member 100 is passed through the central opening 302 of the resilient material sheet 300, and the resilient material sheet 300 is then pulled along the shaft of the male member 100 towards the groin area 104 of the user until it meets the groin area 104 of the user.

An adhesive cover is removed from a plurality of adhesive strips 304 on a back side of the resilient material sheet 300 (FIG. 8), and the plurality of adhesive strips 304 are removably attached to the groin area 104 of the user, which comprises the fifth step of the process involved in wearing the enhanced sexual transmission prevention device. The condom is shown covering the head and shaft of the male member 100, though it does not also cover the scrotum 102 nor extend to the groin area 104 of the user. The resilient material sheet 300, when properly worn (FIG. 5), covers the scrotum 102 and the groin area 104 of the user to provide enhanced sexual transmission prevention. The resilient material sheet 300 also covers the unrolled end of the worn condom 200, so as to prevent the condom 200 from coming off during sexual intercourse.

The plurality of adhesive strips 304 (FIG. 8) may be installed on a back side of the resilient material sheet 300 along a plurality of edges of the resilient material sheet 300. The plurality of adhesive strips 304 may comprise a plurality of adhesive covers so that the adhesive material is not activated prior to use. The plurality of adhesive strips 304 may be any appropriate adhesive strips, such as, for example, surgical tape or medical tape, or any other bioadhesive material that may be removed from a user's skin without causing damage to the skin while leaving little residue.

The illustrations of FIGS. 6 through 9 illustrate an enhanced sexual transmission prevention device. As contemplated by the present disclosure, the enhanced sexual transmission prevention device comprises, generally, a resilient material sheet having a central opening and a plurality of adhesive strips to he worn over a male condom on the male member of a user. The device is intended to be simple, cost effective, and easy to use so that it is not inconvenient for a user to implement such additional sexual transmission prevention.

Figure 6:
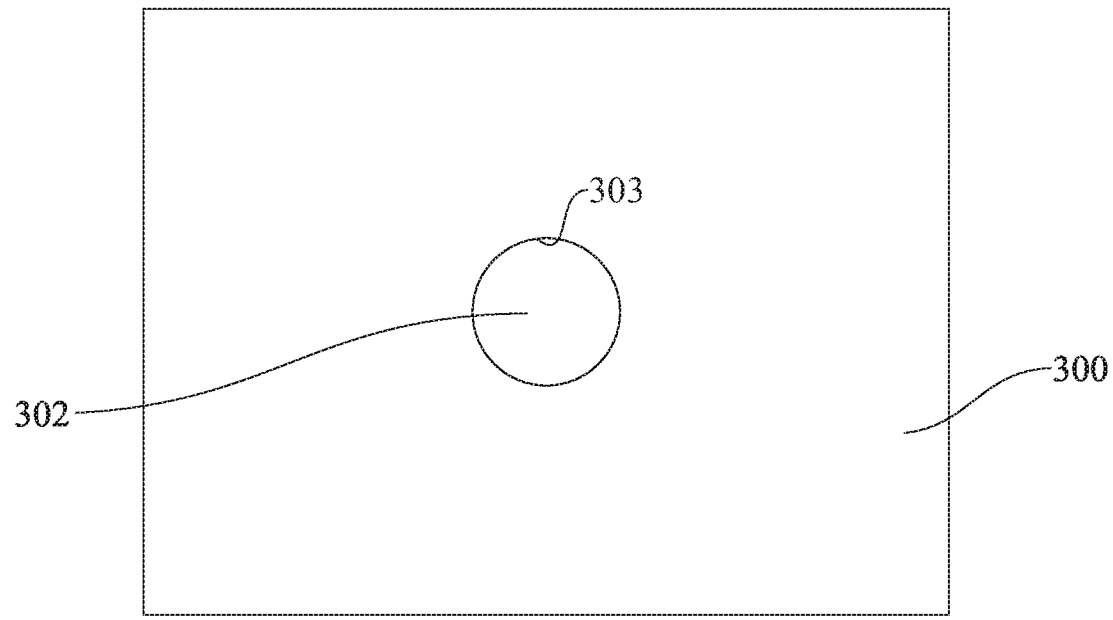
FIG. 6 illustrates a front perspective view of an enhanced sexual transmission prevention device, in accordance with aspects of the present disclosure.

The illustration of FIG. 6 illustrates, in particular, a front perspective view of the enhanced sexual transmission prevention device. The resilient material sheet 300 may be formed as any appropriate geometric shape, though is generally formed as a shape suitable for attachment to the groin area 104 of a user. In one embodiment the shape of the resilient material sheet 300 may be square or rectangular, while in another embodiment the shape of the resilient material sheet 300 may be triangular or circular. In any embodiment, the shape of the resilient material sheet 300 may be sufficient to cover the scrotum 102 and groin area of 104 of the user during sexual intercourse and, in combination with a condom 200, shield the user from sexual transmission.

The resilient material sheet comprises a central opening 302 that includes a resilient circular edge, or rim 303, into which the tip of the male member 100 of a user may be inserted for wearing by the user. The tip of the male member 100 is passed through the central opening 302 of the resilient material sheet 300, and the resilient material sheet 300 is then pulled along the shaft of the male member 100 towards the groin area 104 of the user and may cover the scrotum 102 and the groin area 104 of the user, once properly installed, to provide enhanced sexual transmission prevention.

The central opening 302 may be a die-cut opening that is of smaller diameter than that of a male member 100 of a user so that the central opening 302 is stretched over the shaft of the male member 100. In this way the rolled-up end of a worn condom 200 on the male member 100 is pressed against the groin area 104 of a user to prevent the condom 200 from falling off during sexual intercourse.

Figure 7:
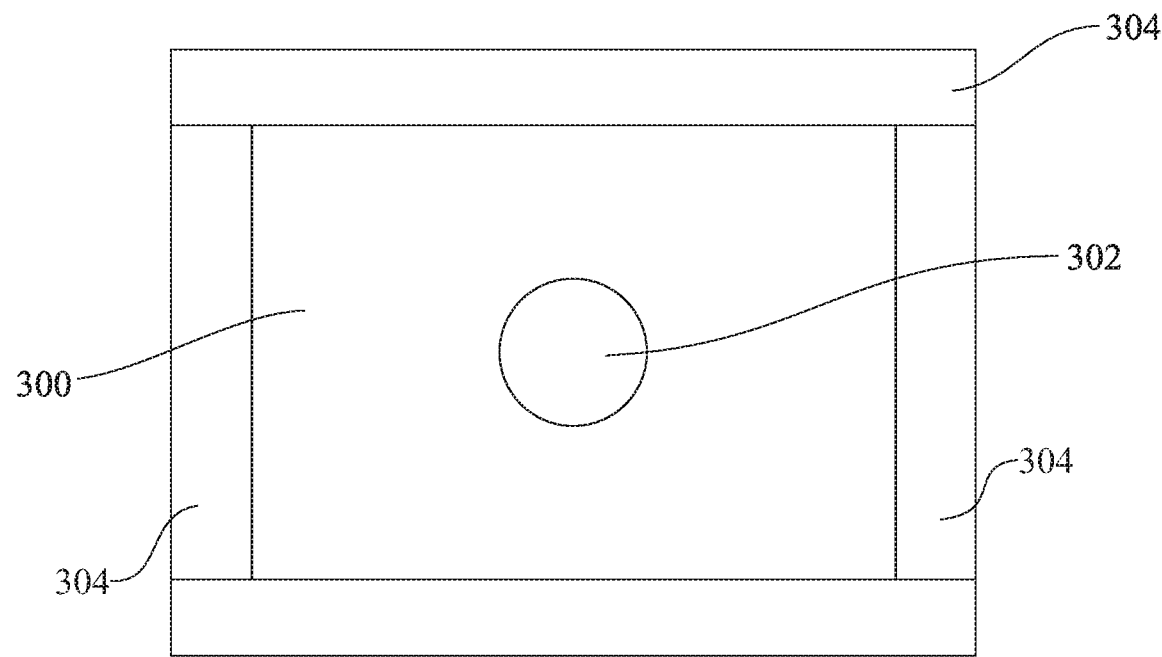
FIG. 7 illustrates a rear perspective view of an enhanced sexual transmission prevention device, in accordance with aspects of the present disclosure.

The illustration of FIG. 7 illustrates, in particular, a rear perspective view of the enhanced sexual transmission prevention device. The plurality of adhesive strips 304 may be installed on a back side of the resilient material sheet 300 along a plurality of edges of the resilient material sheet 300. The plurality of adhesive strips 304 may comprise a plurality of adhesive covers so that the adhesive material is not activated prior to use. The plurality of adhesive strips 304 may be any appropriate adhesive strips, such as, for example, surgical tape or medical tape, or any other bioadhesive material that may be removed from a user's skin without causing damage to the skin while leaving little residue.

Figure 8:
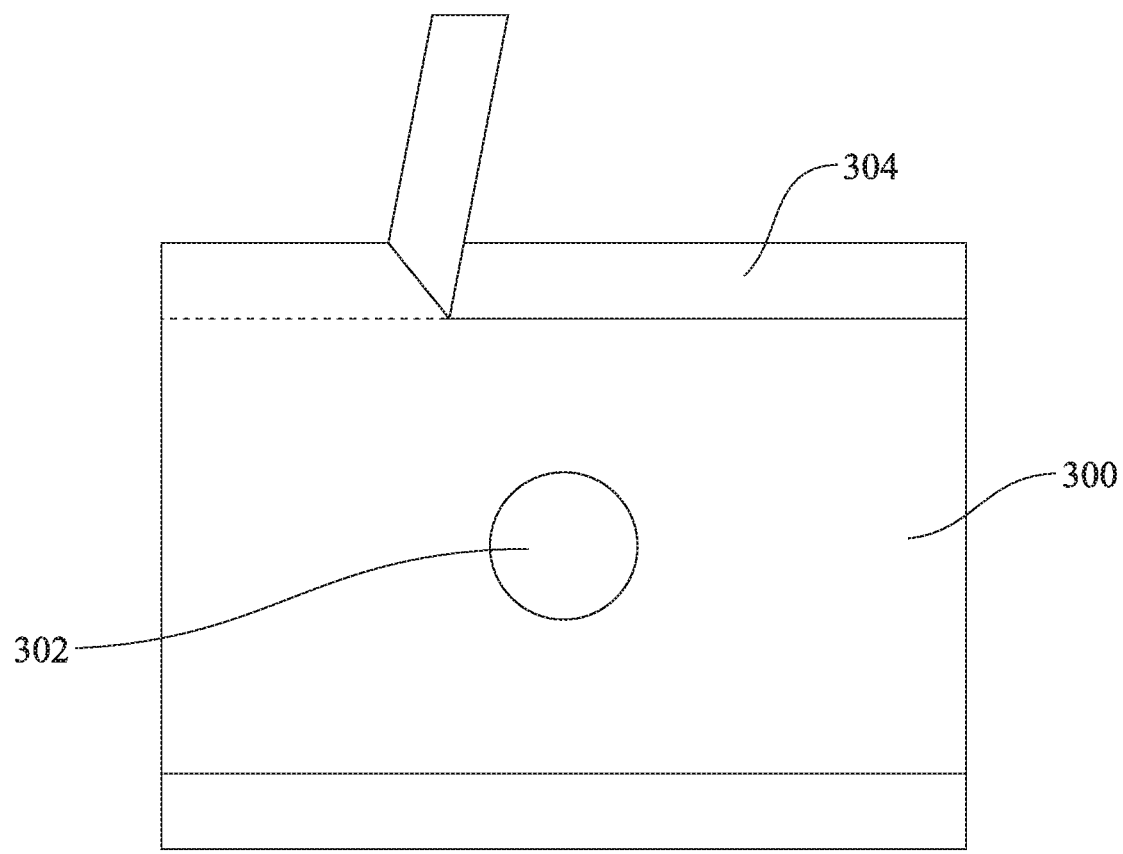
FIG. 8 illustrates removing an adhesive covering from an enhanced sexual transmission prevention device, in accordance with aspects of the present disclosure.

The illustration of FIG. 8 illustrates, in particular, a rear perspective view of the enhanced sexual transmission prevention device with an adhesive strip cover being removed from one of the plurality of adhesive strips 304. The plurality of adhesive strip covers may comprise any appropriate adhesive material covering, which may be any appropriate plastic, or other material, covering adhered to the plurality of adhesive strips.

Figure 9:
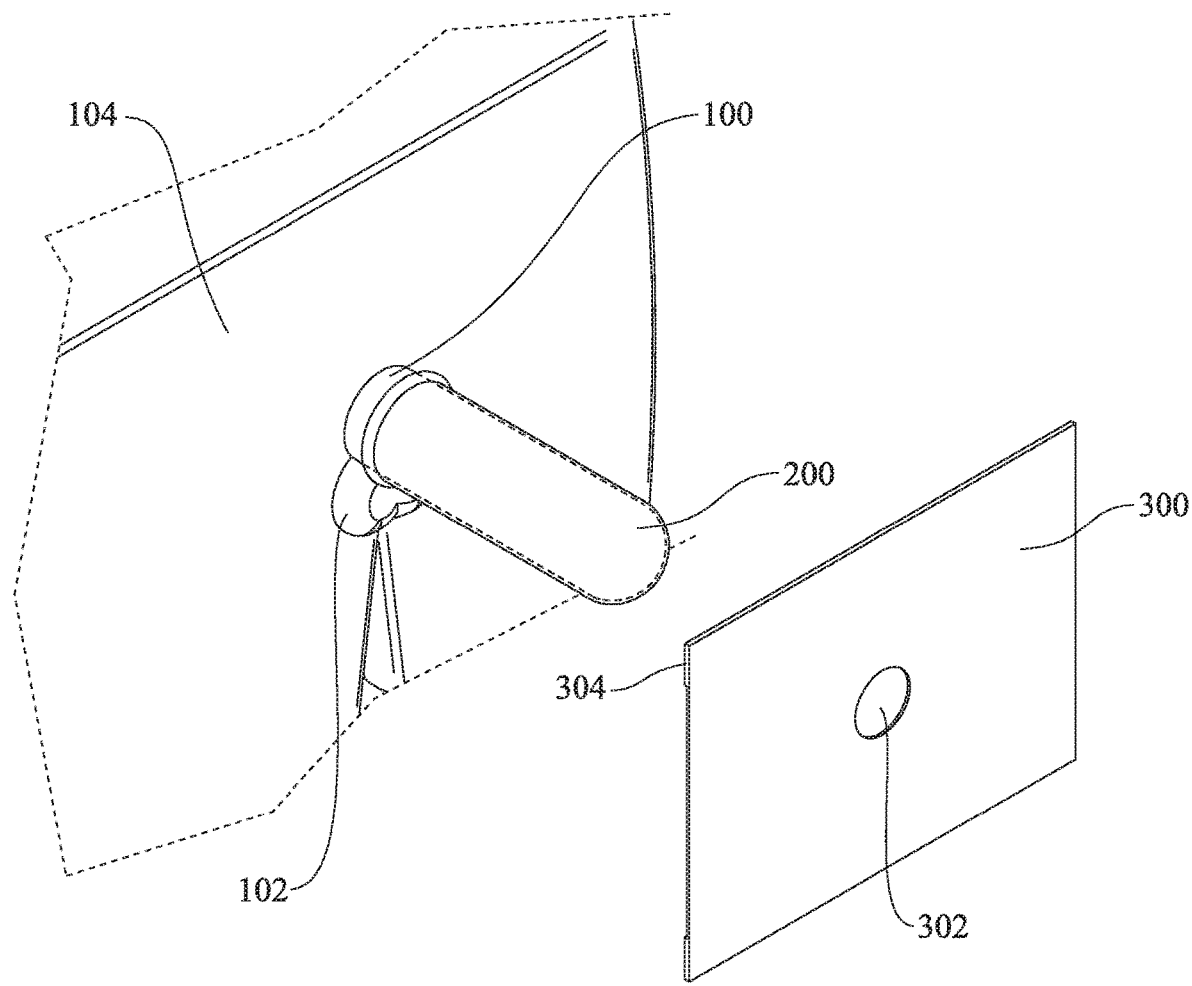
FIG. 9 illustrates an overview of how to use an enhanced sexual transmission prevention device, in accordance with aspects of the present disclosure.

The illustration of FIG. 9 illustrates, in particular, a generic male member 100 from a top isometric perspective view with a worn condom. The male member 100 extends from left to right, with a scrotum 102 illustrated at its base, with both structures attached to a groin area 104 of a user. The condom is shown covering the head and shaft of the male member 100, though it does not also cover the scrotum 102 nor extend to the groin area 104 of the user. The resilient material sheet 300 of the enhanced sexual transmission prevention device is placed near the tip of the male member 100 such that the tip of the male member 100 may be inserted into the central opening 302 of the resilient material sheet 300. The resilient material sheet 300, once installed is intended to cover the scrotum 102 and the groin area 104 of the user to provide enhanced sexual transmission prevention.

The resilient material sheet 300 is pulled towards the groin area 104 of the user and may cover the scrotum 102 and the groin area 104 of the user, once properly installed, to provide enhanced sexual transmission prevention and to prevent the condom 200 from coming off during sexual intercourse.

In some embodiments the enhanced sexual transmission prevention device disclosed herein may be substantially constructed of any suitable material or combination of materials, but typically is constructed of a resilient material or combination of materials such that the combination is resistant to flexing and damage as a result of compression, flexion, or submersion in water. As an example, and without limiting the scope of the present invention, various exemplary embodiments of the combination may be substantially constructed of one or more materials of latex, rubber, polyurethane, animal skin, plastic, or combinations thereof.

As illustrated in FIG. 10, an alternative embodiment of the enhanced sexual transmission prevention device may comprise a garment device 400 such as, for example, male underwear or boxer briefs. In such an embodiment the resilient material sheet 300 may be formed so as to comprise leg openings 402 and to more completely surround the groin area 104 of a user. In such an embodiment the resilient material sheet 300 may still comprise a central opening 302 and the areas of the resilient material sheet 300 covering the groin area 104 of the user may be made of latex, rubber, polyurethane, animal skin, plastic, or combinations thereof, while the remaining areas of the resilient material sheet 300 covering, for example, the hips and buttocks of the user, may be made of a more garment-appropriate material such as, for example, cloth, wool, cotton, denim, or combinations thereof.

In such an alternative embodiment (i.e. as a garment) the resilient material sheet 300 may not comprise a plurality of adhesive strips 304 for attachment to a user, but may, instead, comprise a plurality of straps that may extend around the body of the user. The user may wear such an embodiment by placing their legs through a plurality of leg openings in the enhanced sexual transmission prevention device, wearing the enhanced sexual transmission prevention device around their hips and groin area 104, and then inserting the tip of the male member 100 through the central opening 302 of the resilient material sheet 300. In another embodiment the straps of the resilient material sheet 300 may be removably attached to one another by any appropriate means, such as Velcro, buttons, or hooks, and the straps may be attached to one another behind the user after the resilient material sheet 300 has been placed over the male member 100 of the user.

In conclusion, disclosed is a condom cover (e.g. a sheet) that is pulled over condom on a male member to cover a groin area in a vicinity of the male member. The cover is a separate piece that slides over an erect male member already wearing a condom. The cover has an adhesive back portion to stick to the groin area. Importantly, the cover also holds the base of the condom from slipping off. It does this by having a hole that is much smaller diameter than the male member. The cover could be large enough to cover the scrotum, since STDs may affect that area as well.

In an alternative example, the condom cover concept could be embodied as a garment (e.g. like underwear), and in this example, it does not need the adhesive portion because it would be worn as a garment. As a garment, it could include one or more straps that wrap around the user. This garment concept may be more ergonomic to cover the scrotum than just the sheet embodiment.

The design of the enhanced sexual transmission prevention device is such that the central opening 302 comprises an elastic circumferential interference-fit seal. This feature allows for an easy and gentle installation. This feature also gently holds the condom 200 and resilient material sheet 300 in place. The enhanced sexual transmission prevention device is made of soft, thin sheets that do not rub on the groin area 104 of a user, and can be folded easily for storage and carrying. The design has no raised edges so as not to cause discomfort to the user, and so that the enhanced sexual transmission prevention device is easy to manufacture and use.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. An enhanced sexual transmission prevention device, comprising:
    a removable cylindrical barrier having an exterior wall surface terminating at a thick rim;
    a resilient material sheet having a front side and a rear side;
    a central opening disposed about a center of the resilient material sheet;
        wherein the central opening of the resilient material sheet includes a resilient circular rim that is designed to expand as a member donning the removable cylindrical barrier passes therethrough,
            wherein the resilient circular rim forms an elastic circumferential interference-fit seal with a portion of the exterior wall surface of the cylindrical barrier as the member extends through the central opening; and
    at least one adhesive member disposable on the resilient material.

2. The enhanced sexual transmission prevention device of claim 1, wherein the front side and the rear side of the resilient material sheet define a top edge, a bottom edge, a right side edge and a left side edge.

3. The enhanced sexual transmission prevention device of claim 2, wherein the adhesive member includes a first adhesive strip extending along the top edge of the resilient material sheet and a second adhesive strip extending along the bottom of the resilient material sheet.

4. The enhanced sexual transmission prevention device of claim 3, wherein a third adhesive strip extends along the right side edge of the resilient material and a fourth adhesive strip extends along the left side edge of the resilient material sheet.

5. The enhanced sexual transmission prevention device of claim 4, wherein the first, second, third, and fourth adhesive strip include a removable film.

6. The enhanced sexual transmission prevention device of claim 1, wherein the adhesive member includes at least one adhesive strip disposed about the rear side of the resilient material sheet.

7. The enhanced sexual transmission prevention device of claim 6, wherein the at least one adhesive tape is hypoallergenic, microporous, fluid resistant, and sterile.

8. The enhanced sexual transmission prevention device of claim 1, wherein the central opening of the resilient material sheet is designed to be able to expand to about double in size as the member passes through the central opening and makes contact with the circular rim of the central opening.

9. The enhanced sexual transmission prevention device of claim of 1, wherein the resilient material sheet is integrated to an under garment, the resilient material sheet disposed about a frontal area of the under garment where a scrotum and a male member are located.

10. An enhanced sexual transmission prevention device, comprising:
    a cylindrical barrier having an exterior wall, an interior wall, a closed distal end and an open proximal end including a thick rim;
    a resilient material sheet having a front side and a rear side defining a top edge, a bottom edge, a right side edge and a left side edge;
    a central opening disposed about a center of the resilient material sheet, wherein the central opening of the resilient material sheet includes a resilient circular rim,
        wherein the central opening expands to about double in size when a member donning the cylindrical barrier is inserted through the central opening and the barrier's exterior wall makes contact with the circular rim of the central opening as the member donning the cylindrical barrier passes therethrough, and
        wherein the central opening contracts to form an elastic circumferential interference-fit seal with a portion of the exterior wall surface of the cylindrical barrier as the member extends through the central opening; and a plurality of adhesive strips, wherein the plurality of adhesive strips are disposed about the rear side of the resilient material sheet.

11. The enhanced sexual transmission prevention device of claim 10, wherein the plurality of adhesive strips extend along the top, bottom, right and left side edge of the resilient material sheet.

12. The enhanced sexual transmission prevention device of claim 11, wherein the plurality of adhesive strips each include a removable film.

13. The enhanced sexual transmission prevention device of claim 12, wherein the plurality of adhesive strips are hypoallergenic, microporous, fluid resistant and sterile.

14. The enhanced sexual transmission prevention device of claim 10, wherein the thick rim being of a larger size than the circular rim of the central opening making contact with the rear side of the resilient member, the thick rim being larger size than the circular rim even after the circular rim has increased in size, the thick rim being retained in place at a proximal end of the member and prevented from passing through the central opening of the resilient material sheet.

15. The enhanced sexual transmission prevention device of claim 10, wherein the member donning the barrier is press-fitted through the central opening of the resilient material sheet.

16. A method of using an enhanced sexual transmission prevention device, the method including the steps of:

providing a rolled cylindrical barrier, wherein the barrier comprises an exterior wall, an interior wall, a closed distal end and an open proximal end having a thick rim;

providing a resilient material sheet, wherein the resilient material sheet comprises, a front side and a rear side defining a top edge, a bottom edge, a right side edge and a left side edge, a central opening disposed about a center of the resilient material sheet, wherein the central opening of the resilient material sheet includes a resilient circular rim, and a plurality of adhesive strips, unrolling the rolled cylindrical barrier on a male member until the thick rim of the cylindrical barrier is in close proximity to a proximal end of the member protruding from a user;

sliding the resilient material sheet through the male member donning the barrier by inserting a distal end of the male member through the central opening of the resilient material sheet until the resilient material sheet is proximate to a groin area of the user, wherein the central opening of the resilient members forms an elastic circumferential interference-fit seal with a portion of the exterior wall of the cylindrical barrier as the male member extends through the central opening; and attaching the resilient material sheet to the groin area of the user covering the user's scrotum and surrounding pubic area.

17. The method of claim 16, wherein the central opening of the resilient material sheet capable of expanding to about double in size when the male member donning the barrier is inserted through the central opening and the barrier's exterior wall makes contact with the circular rim of the central opening as the male member passes therethrough.

18. The method of claim 16, wherein the resilient material sheet is attached to the groin using at least four adhesive strips that extend along the front, bottom, right and left edges of the material sheet.

19. The method of claim 16, wherein the thick rim of the cylindrical barrier is of a larger size than the circular rim of the central opening, preventing the thick rim of the cylindrical barrier from passing through the central opening.

20. The method of claim 16, further comprises the step of, removing the resilient material sheet from the groin area, and subsequently removing the cylindrical rollable barrier from the male member of the user.

* * * * *